(12) United States Patent
Lietz

(10) Patent No.: US 6,630,329 B2
(45) Date of Patent: *Oct. 7, 2003

(54) RANDOM TRUNCATION AND AMPLIFICATION OF NUCLEIC ACID

(75) Inventor: Eric Lietz, Santa Cruz, CA (US)

(73) Assignee: Genopsys, Inc., Santa Cruz, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 09/975,754

(22) Filed: Oct. 10, 2001

(65) Prior Publication Data

US 2002/0106677 A1 Aug. 8, 2002

Related U.S. Application Data

(63) Continuation of application No. PCT/US01/07016, filed on Mar. 5, 2001, which is a continuation-in-part of application No. 09/518,335, filed on Mar. 3, 2000, now Pat. No. 6,319,694.

(51) Int. Cl.$^7$ .................... C12F 19/34; C12Q 1/68; C07H 21/04
(52) U.S. Cl. .................. 435/91.2; 435/6; 435/91.1; 435/172.1; 536/24.3; 536/24.33; 800/205; 935/16; 935/17
(58) Field of Search .............. 435/6, 91.1, 91.2, 435/172.1; 536/24.33; 800/205; 935/16, 17

(56) References Cited

U.S. PATENT DOCUMENTS

| | | | |
|---|---|---|---|
| 4,959,312 A | 9/1990 | Sirotkin | 435/91 |
| 5,106,727 A | 4/1992 | Hartley et al. | 435/6 |
| 5,407,813 A | 4/1995 | Gold | 435/91.2 |
| 5,668,294 A | 9/1997 | Meagher et al. | 800/205 |
| 5,853,989 A | 12/1998 | Jeffreys et al. | 435/6 |
| 5,877,305 A | * 3/1999 | Huston et al. | 536/23.53 |
| 5,985,556 A | 11/1999 | Kambara et al. | 435/6 |
| 6,319,694 B1 | * 11/2001 | Lietz | 435/91.2 |

FOREIGN PATENT DOCUMENTS

WO WO-98/42728 1/1998

OTHER PUBLICATIONS

Timothy M. Rose et al., "Consensus–degenerate hybrid oligonucleotide primers for amplification of distantly related sequences", Nucleic Acids Research, 1998, vol. 26, No. 7, XP–002141299, pp. 1628–1635.

Yoshitaka Iba et al., "Expression vectors for the introduction of highly diverged sequences into the six complementarity-–determining regions of an antibody", Gene 194 (1997) 35–46.

* cited by examiner

Primary Examiner—Gary Benzion
Assistant Examiner—Arun K. Chakrabarti
(74) Attorney, Agent, or Firm—Shirley Chen Wilson Sonsini Goodrich & Rosati

(57) ABSTRACT

A method is provided for producing a library of mutagenized polynucleotides from a target sequence comprising (a) taking a sample comprising: (i) a target sequence including a section to be mutagenized, (ii) a library of first primers where the first primers include a first fixed sequence and a first unknown sequence 3' to the first fixed sequence, the first unknown sequence varying within the library of first primers, and (iii) a library of second primers where the second primer include a second fixed sequence that differs from the first fixed sequence, and a second unknown sequence 3' to the second fixed sequence, the second unknown sequence varying within the library of second primers; (b) performing one or more cycles of primer extension amplification on the sample in the presence of at least one polymerase such that a member of the library of the first primers is extended relative to the target sequence; and (c) performing one or more additional cycles of primer extension amplification on the sample such that a member of the library of the second primers is extended relative to the first primer that was extended in step (b) to form the library of mutagenized polynucleotides. The mutagenesis produces a library of mutagenized targeted sequences with random truncations.

33 Claims, 6 Drawing Sheets

Denature in the presence of sense and antisense primers

PCR priming, synthesis resulting in library of randomized gene product

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: 5'-Primer
<221> NAME/KEY: misc_feature
<222> LOCATION: (13)..(21)
<223> OTHER INFORMATION: "n" residues in position 13-21 represent
      adenosine, thymidine, guanosine, cytidine, uridine or inosine.

<400> SEQUENCE: 1
aaaatacata tgnnnnnnnn n                                          21

<210> SEQ ID NO 2
<211> LENGTH: 31
<212> TYPE: DNA
<213> ORGANISM: Artificial Sequence
<220> FEATURE:
<223> OTHER INFORMATION: 3-Primer
<221> NAME/KEY: misc_feature
<222> LOCATION: (23)..(31)
<223> OTHER INFORMATION: "n" residues in position 23-31 represent adenosine,
      thymidine, guanosine, cytidine, uridine or inosine.

<400> SEQUENCE: 2
ataagtgctt cactactaat tannnnnnnn n                               31
```

RANDOM TRUNCATION AND AMPLIFICATION OF NUCLEIC ACID

RELATIONSHIP TO CO-PENDING APPLICATIONS

This application is a continuation of Application No. PCTUS01/07016, filed Mar. 5, 2001, which is a continuation-in-part of U.S. application Ser. No. 09/518,335, filed Mar. 3, 2000 now U.S. Pat. No. 6,319,694, each of which is incorporated herein by reference in its entirety.

FIELD OF THE INVENTION

The present invention relates to methods for mutagenizing nucleic acids and proteins. More particularly, the present invention relates to methods for mutagenizing nucleic acids and proteins relative to an initial target nucleic acid sequence by randomly priming the target sequence during amplification.

BACKGROUND OF THE INVENTION

The sequences of genes encoding many important proteins have been determined at a rapid speed owing to the fast progress in the field of genomics. The three-dimensional structures of thousands of proteins have been determined by X-ray crystallography and other biophysical and biochemical methods, and many more polypeptide sequences critical for the biological function of the proteins have also been determined. However, to a large extent, the correlation between protein primary sequence, tertiary structure, and biological function remains elusive.

Proteins can generally tolerate a certain level of amino acid substitutions without severe consequences on folding or stability (Axe et al., (1996) Proc. Natl. Acad. Sci. USA 93:5590–5594; Bowie et al., (1990) Science 247:1306–1310; Gassner et al. (1996) Proc. Natl. Acad. Sci. USA 93:12155–12158; Baldisseri et al. (1991) Biochem. 30:3628–33; Huang et al. (1996) J. Mol. Biol. 258:688–703.; Rennel et al. (1991) J. Mol. Biol. 222:67–88; Shortle (1995) Curr. Opin. Biotechnol. 6:387–393). On the other hand, for many proteins, a single particular residue can be either critical to function and/or stability (Philippon et al. (1998) Cell Mol. Life Sci. 54:341–346). Although it is desirable to be able to predict protein folding pattern from its primary sequence and to correlate its structure with function in vivo, in reality, this has proven to be a formidable task.

One approach to studying protein structure and function is site-directed mutagenesis. It is an important, but cumbersome approach to compiling an overall picture of protein functional character, let alone stability and regulatory characteristics in vivo. For example, serine beta-lactamases have been found to exhibit very diverse primary structures and catalytic profiles, but almost all of the known three-dimensional structures for serine beta-lactamases exhibit a high degree of similarity with apparently equivalent chemical functionalities in the same strategic positions (Philippon et al. (1998) Cell Mol. Life Sci. 54:341–346).

The apparent complexity of macromolecular structure-function correlation has made random mutagenesis an attractive approach to redesigning proteins. Many of the random mutagenesis methods developed so far are designed to introduce random base-pair substitutions.

Methods of saturation mutagenesis utilizing random or partially degenerate primers that incorporate restriction sites have been described (Hill et al. (1987) Methods Enzymol. 155:558–568; Reidhaar-Olson et al. (1991) Methods Enzymol. 208:564–586; Oliphant et al. (1986) Gene 44:177–183).

Error-prone polymerase chain reaction is another methodology for randomly mutating genes by altering the concentrations of respective dNTP's in the presence of dITP (Leung, S. et al. (1989) Nucleic Acid Res. 17:1177–1195); Caldwell and Joyce (1992) In PCR Methods Application 2:28–33; Spee et al. (1993) Nucleic Acid Res. 21: 777–778).

"Cassette" mutagenesis is another method for creating libraries of mutant proteins (Huebner et al. (1988) Gene 73:319–325; Hill et al. (1987) Methods Enzymol. 155:558–568; Shiraishi and Shimura (1988) Gene 64:313–319; U.S. Pat. Nos. 5,830,720; 5,830,721; 5,830,722; 5,830,728; 5,830,740; 5,830,741; and 5,830,742). Cassette mutagenesis typically replaces a sequence block length of a template with a partially randomized sequence. The maximum information content that can be obtained is thus limited statistically to the number of random sequences in the randomized portion of the cassette.

A protocol has also been developed by which synthesis of an oligonucleotide is "doped" with non-native phosphoramidites, resulting in randomization of the gene section targeted for random mutagenesis (Wang and Hoover (1997) J. Bacteriol. 179: 5812–5819). This method allows control of position selection, while retaining a random substitution rate.

Zaccolo and Gherardi (1999) describe a method of random mutagenesis utilizing pyrimidine and purine nucleoside analogs (Zaccolo and Gherardi (1999) J. Mol. Biol. 285: 775–783). This method was successful in achieving substitution mutations which rendered a □-lactamase with an increased catalytic rate against the cephalosporin cefotaxime. Crea describes a "walk through" method, wherein a predetermined amino acid is introduced into a targeted sequence at pre-selected positions (U.S. Pat. No. 5,798,208).

Methods for mutating a target gene by insertion and/or deletion mutations have also been developed. It has been demonstrated that insertion mutations could be accommodated in the interior of staphylococcal nuclease (Keefe et al. (1994) Protein Sci. 3:391–401). Another insertional mutagenesis method involves a partial fragmentation by a high frequency cutting restriction endonuclease, phosphatasing, and circularizing by appropriate linkers (Fitzgerald et al. (1994) Protein Sci. 3:391–401). Examples of deletional mutagenesis methods developed include the utilization of an exonuclease (such as exonuclease III or Bal31) or through oligonucleotide directed deletions incorporating point deletions (Ner et al. (1989) Nucleic Acids Res. 17:4015–4023).

Methods have also been developed to create molecular libraries as a part of the process of engineering the evolution of molecules with desired characteristics. Termed "directed evolution" or some variant thereof, protocols describing this type of technology typically involve the reassembly of fragments of DNA, representing a "shuffled" pool; in effect, accelerating the recombinatorial process that leads to molecules with desired and/or enhanced characteristics (Stemmer (1994) Nature 370: 389–391; Zhang et al. (1997) Proc. Natl. Acad. Sci. 94: 4504–4509). Such "directed molecular evolution" approaches have been utilized to mutagenize enzymes (Gulik & Fahl (1995) Proc. Natl. Acad. Sci. USA 92: 8140–8144; Stemmer (1994) Nature 370: 389–391;You & Arnold (1996) Protein Eng. 9:77–83; Zhang et al. (1997) Proc. Natl. Acad. Sci. USA. 94:4504–4509), antibodies (Barbas et al. (1994) Proc. Natl. Acad. Sci. USA. 91: 3809–3813; Crameri et al. (1997) Nature Biotech. 15:436–438.), fluorescent proteins (Heim & Tsien (1996) Curr. Biol. 6:178–182.; Siemering et al. (1996) Curr. Biol.

6:1653–1663), and entire operons (Crameri et al. (1996) Nature Med. 2: 100–102).

SUMMARY OF THE INVENTION

The present invention provides methods of random mutagenesis that facilitate random truncation, insertion, deletion and substitution of a target polynucleotide using partially random-sequenced oligonucleotides. The methods can be employed to generate random libraries of polynucleotides and polypeptides which can be screened for clones that exhibit desired biological characteristics (e.g. stability, solubility, catalytic activity, catalytic specificity, binding affinity and specificity, etc.) under specified environment.

In one embodiment, a method is provided for producing mutagenized polynucleotide from a target sequence comprising:
- (a) taking a sample comprising
  - (i) a target sequence including a section to be mutagenized,
  - (ii) a first primer where the first primer includes a first fixed sequence and a first unknown sequence 3' to the first fixed sequence, and
  - (iii) a second primer where the second primer includes a second fixed sequence that differs from the first fixed sequence, and a second unknown sequence 3' to the second fixed sequence;
- (b) performing one or more cycles of primer extension amplification on the sample in the presence of at least one polymerase such that the first primer is extended relative to the target sequence; and
- (c) performing one or more additional cycles of primer extension amplification on the sample such that the second primer is extended relative to the first primer that was extended in step (b) to form the mutagenized polynucleotide.

According to the above method, the first and the second primer may optionally include a portion which is complementary to the target sequence.

Also according to the above method, the first and second unknown sequences refer to the use of a library of first primers and a library of second primers where the first and second unknown sequences vary within the respective libraries of first and second primers. As a result, the sequence of the first and second unknown sequences that are employed in the method are not known in advance to the person performing the method.

In another embodiment, a method is provided for producing a library of mutagenized polynucleotides from a target sequence comprising:
- (a) taking a sample comprising
  - (i) a target sequence including a section to be mutagenized,
  - (ii) a library of first primers where the first primers include a first fixed sequence and a first unknown sequence 3' to the first fixed sequence, the first unknown sequence varying within the library of first primers, and
  - (iii) a library of second primers where the second primer include a second fixed sequence that differs from the first fixed sequence, and a second unknown sequence 3' to the second fixed sequence, the second unknown sequence varying within the library of second primers;
- (b) performing one or more cycles of primer extension amplification on the sample in the presence of at least one polymerase such that a member of the library of the first primers is extended relative to the target sequence; and
- (c) performing one or more additional cycles of primer extension amplification on the sample such that a member of the library of the second primers is extended relative to the first primer that was extended in step (b) to form the library of mutagenized polynucleotides.

According to the above method, each of the first and second primers in the library may optionally include a portion which is complementary to the target sequence.

According to the above method, since the first and second unknown sequences vary within the respective libraries of first and second primers, the sequence of the first and second unknown sequences that are employed in the method are not known in advance to the person performing the method.

In yet another embodiment, a method is provided for producing a library of mutagenized polynucleotides from a target sequence comprising:
- (a) taking a sample comprising
  - (i) a target sequence including a section to be mutagenized,
  - (ii) a library of first primers where the first primers include a first fixed sequence and a first unknown sequence 3' to the first fixed sequence, the first unknown sequence varying within the library of first primers, and
  - (iii) a library of second primers where the second primer includes a second fixed sequence that differs from the first fixed sequence;
- (b) performing one or more cycles of primer extension amplification on the sample in the presence of at least one polymerase such that a member of the library of the first primers is extended relative to the target sequence; and
- (c) performing one or more additional cycles of primer extension amplification on the sample such that a member of the library of the second primers is extended relative to the first primer that was extended in step (b) to form the library of mutagenized polynucleotides.

According to this embodiment, the second fixed sequence of the second primer may be substantially homologous to a portion of the target sequence, such that the resulting library of of mutagenized polynucleotides are amplification products of the target sequence truncated at one end.

Methods are also provided for producing mutagenized polypeptides from a target sequence by forming a library of mutagenized polynucleotides according to any of the above methods and expressing polypeptides from the library of mutagenized polynucleotides.

According to any of the above methods, the target sequence may have a sequence which is known or partially or completely unknown.

According to any of the above methods, the target sequence may have a sequence which is known or partially or completely unknown. Optionally, the target sequence is a DNA sequence encoding a portion of an antibody such as the complementarity-determining region (CDRs, e.g. the variable regions of the heavy chain or the light chain), and more preferably a single chain antibody including the variable regions of the heavy chain and the light chain of an antibody.

According to any of the above methods, the target sequence may be a member of a library of DNA sequences that have conserved regions and hypervariable regions. For example, the target sequence is a member of a library of DNA sequences encoding an antibody library, in particular, a single chain antibody library.

Also according to any of the above methods, each of the first and second fixed sequences preferably include at least one restriction site, which facilitates subcloning in an expression vector, and the ultimate synthesis of RNA and polypeptides from the polynucleotides produced according to the methods. The synthesis of RNA and polypeptides can be performed in vitro or in vivo via in transformed or transfected host cells.

Also according to any of the above methods, one of the first and second fixed sequences may include a "start" codon sequence (e.g. ATG or GTA) and the other of the first and second fixed sequence may include a sequence encoding one or more translation stop codons.

Also according to any of the above methods, the lengths of the first and second primers may optionally be between 10 and 80 nucleotides, preferably between 12 and 60 nucleotides and more preferably between 15 and 40 nucleotides. Optionally, the first and second primers may include one or more inosines at the 3' end penultimate and ultimate positions.

Also according to any of the above methods, the unknown sequences are preferably at least partially unknown. More specifically, a first portion of the unknown sequences may be fixed within the library and a portion may vary within the library. In a preferred embodiment, the unknown sequence further includes a sequence encoding one or more specific amino acid residues such as the conserved amino acid residues of the protein encoded by the target sequence.

The unknown sequences of the first and second primers may optionally be synthetic and may be synthesized by randomly incorporating A, T, G, C, I or U.

The first and second unknown sequences in the above methods preferably have a length between 3 and 70 nucleotides, more preferably between 4 and 50 nucleotides, and most preferably between 5–15 nucleotides.

Also according to any of the above methods, the sample preferably includes the first primer at a concentration approximately equivalent to the concentration of the second primer. The concentrations of the first and second primers are each independently preferably between about 0.01 and 100 $\mu$M, more preferably between about 0.1 and 10 $\mu$M, and most preferably between about 0.2–1.0 $\mu$M.

Also according to any of the above methods, the sample preferably includes salts such as NaCl and $Mg^{2+}$ or any other components which facilitate desirable reaction characteristics.

Also according to any of the above methods, at least a portion of the multiple cycles of primer extension polymerase amplification may be performed such that extension by the polymerase is at least partially performed at a temperature below 70° C. for at least 30 sec.

Also according to any of the above methods, at least a portion of the multiple cycles of primer extension polymerase amplification may be performed such that extension by the polymerase is at least partially performed at a temperature below 60° C. for at least 30 sec.

Also according to any of the above methods, at least a portion of the multiple cycles of primer extension polymerase amplification may be performed such that extension by the polymerase is at least partially performed at a temperature below 50° C. for at least 30 sec.

Also according to any of the above methods, at least a portion of the multiple cycles of primer extension polymerase amplification may be performed such that extension by the polymerase is performed by heating the amplification reaction mixture from a temperature between about 30° C. to 60° C. to a temperature between about 65° C. to 75° C. for at least 30 sec.

Also according to any of the above methods, at least a portion of the multiple cycles of primer extension polymerase amplification may be performed by ramping the temperature about 30° C. to 60° C. to a temperature between about 65° C. to 75° C. for at least 1 min.

Also according to any of the above methods, at least a portion of the multiple cycles of primer extension polymerase amplification may be performed by ramping the temperature about 30° C. to 60° C. to a temperature between about 65° C. to 75° C. for at least 1 min, wherein the incubation time after each ramp is shorter than that of the previous ramp.

Also according to any of the above methods, it is noted that the first and second primer may anneal to any portion of the target sequence. After at least one cycle of primer extension amplification, a truncated sequence of the target sequence is synthesized. When libraries of the first and second primers are included in the amplification reaction, truncated sequences of various lengths can be synthesized after at least one cycle of primer extension amplification.

Also according to any of the above methods, it is noted that the random sequence included in the first and second primer may anneal to the target sequence to form an imperfect double-stranded sequence during the at least one cycle of primer extension amplification. Such an imperfect double-stranded sequence may include mismatches, bulges or loops which may result in insertion, deletion and substitution of the target sequence.

Also according to any of the above methods, it is noted that the library of mutagenized polynucleotides formed may include homologs of the truncated sequences of the target sequence which include at least two sequences from the library of the first or second primers.

Also according to any of the above methods, it is noted that the library of mutagenized polynucleotides formed may include homologs of the truncated sequences of the target sequence where at least two portions of the truncated sequences of the target sequence have been deleted.

Also according to any of the above methods, it is noted that the library of mutagenized polynucleotides formed may include homologs of the target sequence where at least a portion of the mutagenized polynucleotides have been mutagenized at one or more separate locations on the target sequence.

The present invention also relates to reagents for performing the various methods of the present invention. For example, the reagents may be a first primer, a library of first primers, a second primer, and a library of second primers. The present invention may also include other reagents disclosed herein.

The present invention also relates to kits for performing the various methods of the present invention. The kits may include any two or more reagents employed in these methods, including, for example, a first primer, a library of first primers, a second primer, a library of second primers, one or more polymerases, and other reagents and buffers which may be used to employ these methods. In one embodiment, the kit includes a first primer and a second primer. In another embodiment, the kit includes a library of first primers and a library of second primers.

BRIEF DESCRIPTION OF THE FIGURES

FIG. 3A illustrates a temperature profile where after the denaturation of the mixture, the oligonucleotides are allowed to anneal to the target at a sufficiently low temperature and the annealing temperature is then gradually raised until reaching the optimum temperature for the polymerase.

FIG. 3B illustrates a temperature profile where the annealing temperature is raised by combining gradual rise with ramping.

FIG. 3C illustrates a temperature profile where the annealing temperature is raised by several ramps or in a step-wise manner where the incubation time after each ramp/step is shorter than previous one.

DETAILED DESCRIPTION OF THE INVENTION

Figure 1:
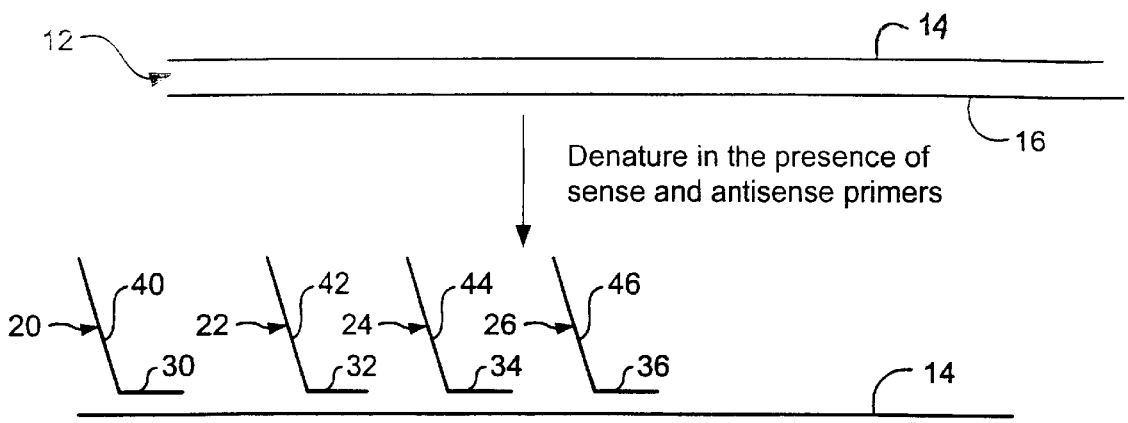
FIG. 1 schematically illustrates mutagenesis of a gene sequence (target sequence) using libraries of first and second primers which result in truncation, insertion, deletion and substitution of the target gene sequence in the primer extension amplification products.
Figure 1:
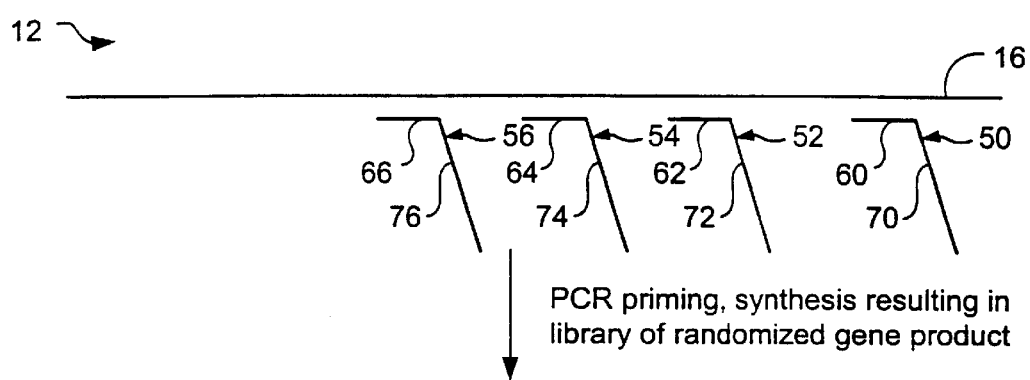

The present invention provides methods for generating a library of mutagenized polynucleotides from a target sequence. Any gene sequence can serve as the target sequence and be mutagenized according to the methods of the present invention to yield a large and diverse population of mutagenized polynucleotides having some degree of homology to the target sequence. These polynucleotides can then be subcloned into expression vectors to produce proteins with diverse structures, biophysical characteristics, and biological functions relative to the protein encoded by the target sequence.

According to the present invention, multiple cycles of primer extension amplification are performed on a sample including the template target sequence to be mutagenized. In one embodiment, a method is provided for producing mutagenized polynucleotides from a target sequence in a sample. The sample includes a target sequence to be mutagenized, a first primer including a first fixed sequence and an unknown sequence 3' to the first specified sequence, and a second primer including a second fixed sequence and an unknown sequence 3' to the second specified sequence. The second fixed sequence is different from the first fixed sequence.

Amplification is conducted under conditions such that the first or second primer anneals to a portion of the target sequence and be extended relative to the target sequence. After at least one cycle of primer extension amplification, truncated sequences of the target sequence are synthesized.

In another embodiment, a method is provided for producing mutagenized polynucleotides from a target sequence in a sample. The sample includes a target sequence to be mutagenized, a library of first primers and a library of second primers. The first primer includes a first fixed sequence and a first unknown sequence 3' to the first specified sequence, the first unknown sequence varying within the library of first primers. The second primer includes a second fixed sequence that differs from the first fixed sequence, and a second unknown sequence 3' to the second fixed sequence, the second unknown sequence varying within the library of second primers.

In the presence of these libraries of the first and second primers in the amplification reaction, each first and second primer anneals randomly to different portions of the target sequence. As a result, truncated sequences of various lengths may be synthesized after at least one cycle of primer extension amplification.

Some portions of the resulting truncated sequences may be partially homologous to a portion of the target sequence and may therefore serve as new primers or new templates in subsequent cycles of primer extension amplification. These new primers form an imperfect double-stranded sequence with the target sequence during amplification and are extended. The imperfect double-stranded sequence formed with the target sequence during amplification can include mismatches, bulges or loops in the primer and/or template target sequence. After multiple amplification cycles, the extended oligonucleotide forms an amplification product which is a homolog of the target sequence where all or a portion of the sequence of the oligonucleotide has been introduced into the target sequence. Depending on the imperfect double-stranded sequence formed, the amplification product may correspond to an insertion, deletion, truncation, or substitution of a portion or portions of the target sequence. As a result, a greater variety of sequences are generated, including sequences of various lengths and incorporating portions of the target sequence after mutations such as insertion, deletion, truncation and substitution.

By using primers that incorporate a sequence that is unknown at the time of primer extension amplification (the unknown sequence), for example by using random sequences, it is possible to conduct amplifications which are less carefully controlled. This allows random libraries of sequences to be used as the 5' and 3' primers and obviates the need to custom design the primers relative to the target sequence. Meanwhile, the fixed sequences of the primers that are incorporated into the final amplification products may serve as convenient subcloning sites and/or translation initiation and stop sites in subsequent genetic manipulations. Since the range of primers that may be used may not limited by one's ability to custom synthesize particular sequences, the sequence space and molecular diversity of the resulting library of mutagenized polynucleotides and polypeptides is significantly enlarged. Alternatively, it may be desirable to synthesize only those primers that are less susceptible to intramolecular interactions (e.g. hairpins). It is may also be possible to weed out primer sequences that may be difficult to be denatured due to intramolecular interactions.

A further feature of the present invention is that one need not know the location where the first and second primers anneal to the target sequence during amplification. Instead, the unknown sequence on the primers may form base pairs with the target gene sequence wherever is suitable under the amplification conditions. This departure from a controlled mutagenesis approach allows the range of oligonucleotides that may be used to be significantly increased beyond what one can custom synthesize, simplifies the planning and time required to create the mutagenized polynucleotides, and ultimately increases the molecular diversity of the resulting library of mutagenized polynucleotides and polypeptides.

Yet a further feature of the present invention is that multiple unknown sequences can be incorporated into the target sequence via insertion, deletion and substitution. This results in further enhanced heterology between the mutagenized polynucleotides and the original target gene.

Yet a further feature of the present invention is that different libraries of mutagenized polynucleotides can be generated from the same group of primers. The first and second unknown sequences on the primers anneal to the target sequence at locations which depend upon the homology of the unknown sequence to a given section of the target sequence and the conditions of the amplification. By varying the amplification conditions (such as annealing temperature, salt concentration, or other factors), different primers with different unknown sequences anneal to the target sequence, in different ways, and at different locations. These different forms of annealing control what insertions, deletions, or changes (substitutions or point mutations) in the target sequence occur during the amplification cycles. As a result, one is able to vary and control the degree of random incorporated mutations such as product length, insertion, deletion, and substitution by controlling the amplification conditions and achieve different degrees of mutagenicity.

According to one embodiment of the method, a sample is formed which comprises (i) a target sequence including a section to be mutagenized, (ii) a first primer comprising a first fixed sequence and a first unknown sequence 3' to the first fixed sequence, and (iii) a second primer comprising a second fixed sequence that differs from the first sequence, and a second unknown sequence 3' to the second fixed sequence. At least one cycle of primer extension amplification is performed on the sample in the presence of at least one polymerase such that the first primer or second primer anneals to either the sense or antisense strand of the section of the target sequence and is extended by the polymerase. Additional cycles of primer extension amplification are then performed on the sample to form a mutagenized double-stranded polynucleotide comprising sequences of the first and second primers.

The first and second unknown sequence may be a completely random sequence which is unknown at the time of primer extension amplification. The first and second fixed sequences may include a portion that is complementary or partially complementary to the target sequence.

For example, the first and second primers may anneal to the antisense and sense strand of the target sequence, respectively, to form an imperfect double-stranded sequence and be extended by the polymerase. After at least one cycle of primer extension amplification is performed, a truncated version of the target sequence is produced which incorporates the first and second primers. Additional cycles of primer extension amplification are then performed on the sample to form mutagenized double-stranded polynucleotides comprising sequences of the first and second primers which are extended by the polymerase. The mutagenized double-stranded polynucleotides formed during the method can differ from the target sequence in one or more locations and can include insertions, deletions, and/or substitutions of one or more oligonucleotides.

The above embodiment may be extended to where libraries of first and second primers are employed. For example, a method is also provided which includes taking a sample comprising (i) a target sequence including a section to be mutagenized, (ii) a library of first primers wherein first primer includes a first fixed sequence and a first unknown sequence 3' to the first specified sequence, the unknown unknown sequence varying within the library of first primers, and (iii) a library of second primers wherein the second primer includes a second fixed sequence that differs from the first fixed sequence, and a second unknown sequence 3' to the second specified sequence, the second unknown sequence varying within the library of second primers. One or more cycles of primer extension amplification are performed on the sample in the presence of at least one polymerase such that a member of the library of the first primers is extended relative to the target sequence. One or more additional cycles of primer extension amplification are performed on the sample such that a member of the library of the second primers is extended relative to the first primer that was extended to form the library of mutagenized polynucleotides.

The first and second primers may anneal to the target sequence or amplification products thereof to form imperfect double-stranded sequences and be extended by the polymerase. As a result, after multiple amplification cycles, a library of mutagenized polynucleotides at various lengths are produced as amplification products that can be truncated versions of the target sequence incorporating mutations such as insertions, deletions and/or substitutions in one or more locations.

As noted above, one need not know the unknown sequence of the first and/or second primers used in the method or where and how the primers anneal to the target sequence during amplification. In that regard, it is also not necessary to know the sequence of the target sequence prior to performing the method. The first and second unknown sequences on the first and second primers in the libraries may anneal to any portions of the target sequence under suitable conditions and be extended during cycles of the primer extension amplification. As a result, a library of amplification products are generated that incorporate various mutations.

Optionally, the unknown sequences may be at least partially unknown. More specifically, a first portion of the unknown sequences may be fixed within the library and a portion may vary within the library. In a preferred embodiment, the unknown sequence further includes a sequence encoding one or more specific amino acid residues such as the conserved amino acid residues of the protein encoded by the target sequence.

In yet another embodiment of the present invention, a method is provided for producing a library of mutagenized polynucleotides that are amplification products of the target sequence truncated at one end of the target sequence. The method includes taking a sample comprising: (i) a target sequence including a section to be mutagenized, (ii) a library of first primers where the first primers include a first fixed sequence and a first unknown sequence 3' to the first fixed sequence, the first unknown sequence varying within the library of first primers, and (iii) a library of second primers where the second primer include a fixed sequence that differs from the first fixed sequence. One or more cycles of primer extension amplification are performed on the sample in the presence of at least one polymerase such that a member of the library of the first primers is extended relative to the target sequence. One or more additional cycles of primer extension amplification on the sample such that a member of the library of the second primers is extended relative to the first primer that was extended in step (b) to form the library of mutagenized polynucleotides.

According to this embodiment, the second primer may include a fixed sequence that is substantially homologous to a portion of the target sequence. After multiple amplification cycles, a library of of mutagenized polynucleotides are produced that include amplification products of the target sequence truncated at one end of the target sequence.

Once the mutagenized polynucleotides are generated by the above-described methods, the mutagenized polynucleotides can be further subcloned into suitable expression vectors after restriction digestion or direct cloning of PCR products. The proteins encoded by the mutagenized polynucleotides can be expressed in prokaryotic or eukaryotic expression systems. The biological functions of the expressed proteins can then be screened and proteins with altered, preferably improved, biological characteristics selected, depending on the trait(s) that are desirable under specified environmental conditions. Thus, the present invention provides powerful tools for generating large libraries of polynucleotides and their corresponding polypeptides, which can be screened for diverse structures and functions. Also, important functional domain components (e.g. catalytic, binding, etc.) can be identified from within a gene or gene product.

Unlike cassette mutagenesis where a sequence block of a single template is typically replaced by a partially randomized sequence, the present invention enables one to generate a library of mutagenized polynucleotides where the sequence of the target sequence has been altered at multiple locations, thus generating a much larger and more diverse library of randomized sequences. In addition, by using the first and second primers that are designed to incorporate desired restriction sites, translation start or stop codons, the resulted library of mutagenized oligonucleotides can be efficiently subcloned into expression vectors and a library of polypeptides encoded by the mutagenized target sequences can be expressed.

The synthesis of a large library of polynucleotides relative to the target sequence has a wide variety of applications. For example, the mutagenized polynucleotides can be used to screen for novel nucleic acid (DNA or RNA) therapeutics that can act as ligands for a protein such as aptamers, or for novel ribozymes that can act as efficient enzymes for various substrates. Viral genes encoding critical regulatory proteins can be mutagenized and screened for transdominant inhibitors that can be developed into more specific and efficacious antiviral therapeutics such as for gene therapy. Viral genomes can also be mutagenized and screened for more potent viral vaccines such as DNA vaccines.

Further, the proteins encoded by the library of mutagenized target sequences can be screened for various novel functions or optimized functions. For example, genes encoding important enzymes can be mutagenized and the corresponding expressed proteins can be screened for novel binding affinity to a target molecule, for improved catalytic activity, thermal stability, substrate specificity, ligand binding affinity, etc.

For industrial enzymes, environmental conditions may be radically different from the physiological or native environment, some of which may seem to be too harsh for the normal function of native enzymes, such as high temperature and alkalinity. By using the methods of the present invention, a target enzyme may be extensively and dramatically mutated in order to identify homologs of the protein that have superior thermal stability or resistance to harsh environmental elements.

Therapeutic antibodies, cytokines and growth factors can also be mutagenized and screened for characteristics such as improved shelf stability, functional stability, solubility, pharmacokinetics, higher in vivo activity, and reduced side effects. Genomes of microorganisms can be mutagenized and screened for industry applications such as chemical and drug processing, oil spill clean-ups and pollution treatment.

The present invention will now be described in relation to the figures. FIG. 1 illustrates an embodiment in which a sample is formed which includes a target sequence 12 having antisense 14 and sense 16 strands. Also included in the sample is a library of first primers 20, 22, 24, and 26, each including an unknown sequence, 30, 32, 34, 36, respectively, that are capable of annealing to various portions of the antisense strand 14 of the target sequence 12 to form imperfect double-strands. Each of the first primers in the library, 20, 22, 24, and 26, includes a fixed sequence 40, 42, 44, and 46, respectively, which may contain a restriction site and a translation start codon.

Also included in the sample is a library of second primers 50, 52, 54, and 56, each including an unknown sequence, 60, 62, 64, 66, respectively, that are capable of annealing to various portions of the sense strand 16 of the target sequence 12 to form imperfect double-strands. Each of the first primers in the library, 50, 52, 54, and 56, includes a fixed sequence 70, 72, 74, and 76, respectively, which may contain a restriction site and one or more translation stop codon(s).

After combining the reaction components, the sample is heated to a temperature which is sufficiently high to denature all the sequences in the sample (e.g. about 95° C.). The sample is then cooled, typically to a temperature below 60° C. Upon cooling, the first primers, 20, 22, 24, and 26, and the second primers, 50, 52, 54, and 56, anneal to the target sequence. The first and second unknown sequences of the first and second primers may not be perfectly complementary to the target sequence and therefore form imperfect double-stranded sequences including mismatches, bulges and internal loops. When incubated in the presence of at least one polymerase (e.g. a thermal stable polymerase such as Taq), the first and second primers are extended along the target sequence to form extended sequences.

After multiple cycles of primer extension amplification, sequences that are truncated versions of the target sequence are synthesized and amplified. Meanwhile, the imperfect double-stranded sequences formed between the unknown sequences and the target sequence facilitate incorporation of random mutations (e.g., insertion, deletion and substitution) into the final amplification products.

It is noted that different sets of the first and/or second primers in the library may anneal to the target sequence depending on the homology between the target sequence (template) and any proximal oligonucleotide primer, as well as the annealing/amplification conditions. For example, at one temperature, a first set of the first primers anneal while at a second, lower temperature, a broader range of the first primers anneal to the target sequence. As can be seen from FIG. 1, a very wide array of polynucleotides can be generated depending on what primers are present in the sample and the number of amplification cycles that are performed.

Once a library of mutagenized polynucleotides are formed, for example as illustrated in FIG. 1, mutagenized polypeptides may be formed from the mutagenized polynucleotides. For example, the library of mutagenized polynucleotides may be cloned into an appropriate expression vector, and the resulting vector may be used to transform, transfect or transduce a host cell to produce the mutant proteins. The mutant proteins can then be screened for desired characteristics.

1. Target Sequence

The target sequence can be any sequence. For example, the target sequence can be a gene (either wild-type or mutant), a strand of synthetic DNA oligonucleotide, or an RNA from viruses or cellular extracts. The target sequence can be single- or double-stranded, present as linear nucleotides or residing in a section of a circularized plasmid. The sequence of the target sequence may be known or only partially known. Examples of target sequences with partially known sequences include a linear or circular target sequence that has sections of known sequences flanking an unknown sequence. The unknown sequence may be a full length or a truncated fragment of a gene and this gene may be mutagenized by using primers homologous to the flanking sections with known sequences.

Single-stranded mRNA or the RNA genomes of certain viruses can be converted to DNA by reaction with reverse transcriptase (RT). The product of the reverse transcriptase reaction may then be amplified by using polymerase chain reaction (RT-PCR) and used as a target sequence.

In one embodiment, the target sequence is a DNA sequence encoding a portion of an antibody such as the complementarity-determining region (CDR, e.g. the variable regions of the heavy chain or the light chain), and more preferably a single chain antibody including the variable regions of the heavy chain ($V_H$) and the light chain ($V_L$) of an antibody.

A typical antibody contains four polypeptides-two identical copies of a heavy (H) chain and two copies of a light (L) chain, forming a general formula $H_2L_2$. Each L chain is attached to one H chain by a disulfide bond. The two H chains are also attached to each other by disulfide bonds. Papain cleaves N-terminal to the disulfide bonds that hold the H chains together. Each of the resulting Fabs consists of an entire L chain plus the N-terminal half of an H chain; the Fc is composed of the C-terminal halves of two H chains. Pepsin cleaves at numerous sites C-terminal to the inter-H disulfide bonds, resulting in the formation of a divalent fragment [F(ab')] and many small fragments of the Fc portion. IgG heavy chains contain one N-terminal variable ($V_H$) plus three C-terminal constant ($C_H1$, $C_H2$ and $C_H3$) regions. Light chains contain one N-terminal variable ($V_L$) and one C-terminal constant ($C_L$) region each. The different variable and constant regions of either heavy or light chains are of roughly equal length (about 110 amino residues per region). Fabs consist of one $V_L$, $V_H$, $C_H1$, and $C_L$ region each. The $V_L$ and $V_H$ portions contain hypervariable segments (complementarity-determining regions or CDR) that form the antibody combining site.

The $V_L$ and $V_H$ portions of a monoclonal antibody can also be linked by a synthetic linker to form a single chain protein (scFv) which retains the same specificity and affinity for the antigen as the monoclonal antibody itself. Bird, R. E., et al. (1988) "Single-chain antigen-binding proteins" Science 242:423–426. A typical scFv is a recombinant polypeptide composed of a $V_L$ tethered to a $V_H$ by a designed peptide, such as $(Gly_4\text{-}Ser)_3$, that links the carboxyl terminus of the $V_L$ to the amino terminus of the $V_H$ sequence. The construction of the DNA sequence encoding a scFv can be achieved by using a universal primer encoding the $(Gly_4\text{-}Ser)_3$ linker by polymerase chain reactions (PCR). Lake, D. F., et al. (1995) "Generation of diverse single-chain proteins using a universal $(Gly_4\text{-}Ser)_3$ encoding oligonucleotide" Biotechniques 19:700–702.

The method of the present invention can be used to randomize one or more portions of the antibody sequence, especially the single chain antibody. By using a first and second primers that have sequences homologous to sequences flanking a specific portion of the antibody sequence, such as the variable regions of the heavy chain and the light chain, the sequence flanked by the first and second primers can be mutagenized to include insertions, deletions and point-mutations (or substitutions) in this region. The mutagenized antibody sequences can then be screened for altered functions of the original single chain antibody, such as improved binding affinity to its cognate antigen or other desirable functions (e.g. enhanced enzyme-like efficiency).

Optionally, a library of DNA sequences may serve as the target sequences to be mutagenized by using the method of the present invention. For example, a library of single chain antibody sequences that are selected from a high throughput screening method such as phage display may be used as the target sequences. By using a first and second primers that have sequences homologous to the constant regions flanking the variable region of the heavy chain or the light chain, the variable sequences of the antibody library can be further mutagenized to include random truncations in this region. Since drastic mutations can be facilitated by using the method of present invention, the sequence space and the diversity of the antibody library can be increased tremendously.

This highly complex library of the mutagenized antibody sequences can then be screened for desirable functions of antibodies, such as improved binding affinity to their cognate antigens, reduced binding affinity to undesirable antigens (to avoid side effects), or enhanced enzyme-like efficiency.

2. First and Second Primers

The first and second primers may serve as upstream (5') and downstream (3') primers which flank a section of the target sequence. After at least one cycle of primer extension, the resulting product can be a truncated version of the target sequence.

The first and second primers include a fixed sequence and an unknown sequence. The fixed sequence preferably includes at least one restriction site as well as a tail composed of a number of bases; the number dictated by the restriction enzyme as required for efficient cleavage. Such sites would allow, for example, cloning of amplification products into a vector having the matching restriction sites. The fixed sequence may also include transcription promoter sequences (e.g. TATA boxes) or RNA polymerase terminator sequences to allow efficient transcription of the amplification products.

The first and second primers may optionally include one or more inosines at the 3' end penultimate and ultimate positions to enhance binding and elongation efficiency. It is believed that since inosine is capable of base-pairing to any phosphoramidite base, the efficiency of annealing/extension can be enhanced by inclusion of inosines at the 3' end of the random portion of the annealing primers. The incorporation of inosines at the 3' ultimate and penultimate positions would thus enhance base pair hydrogen bonding, as well as polymerase function at this extension end of the oligonucleotide primer/template complex.

The fixed sequence of the first and/or second primer may also include sequence elements that facilitate desirable transcriptional and/or translational characteristics, or desirable transcription and/or translation product characteristics. These characteristics may include elements that facilitate screening, labeling, isolation and/or purification (e.g. His tags), or structural components that facilitate intended inter- or intramolecular interactions.

The fixed sequence of the first primer preferably includes a restriction site that incorporates a translational start codon, such as NdeI or NcoI. A NdeI site includes an ATG sequence and may be useful for subsequent subcloning and expression in Gram-negative bacterial hosts recognizing ATG as a start codon. A NcoI site includes a GTA sequence and may be useful for subsequent subcloning and expression in Gram-positive bacterial hosts.

The fixed sequence of the second primer preferably includes a translational a stop codon such as TAA, TGA or TAG, in at least one, and preferably all three reading frames.

Figure 2A:
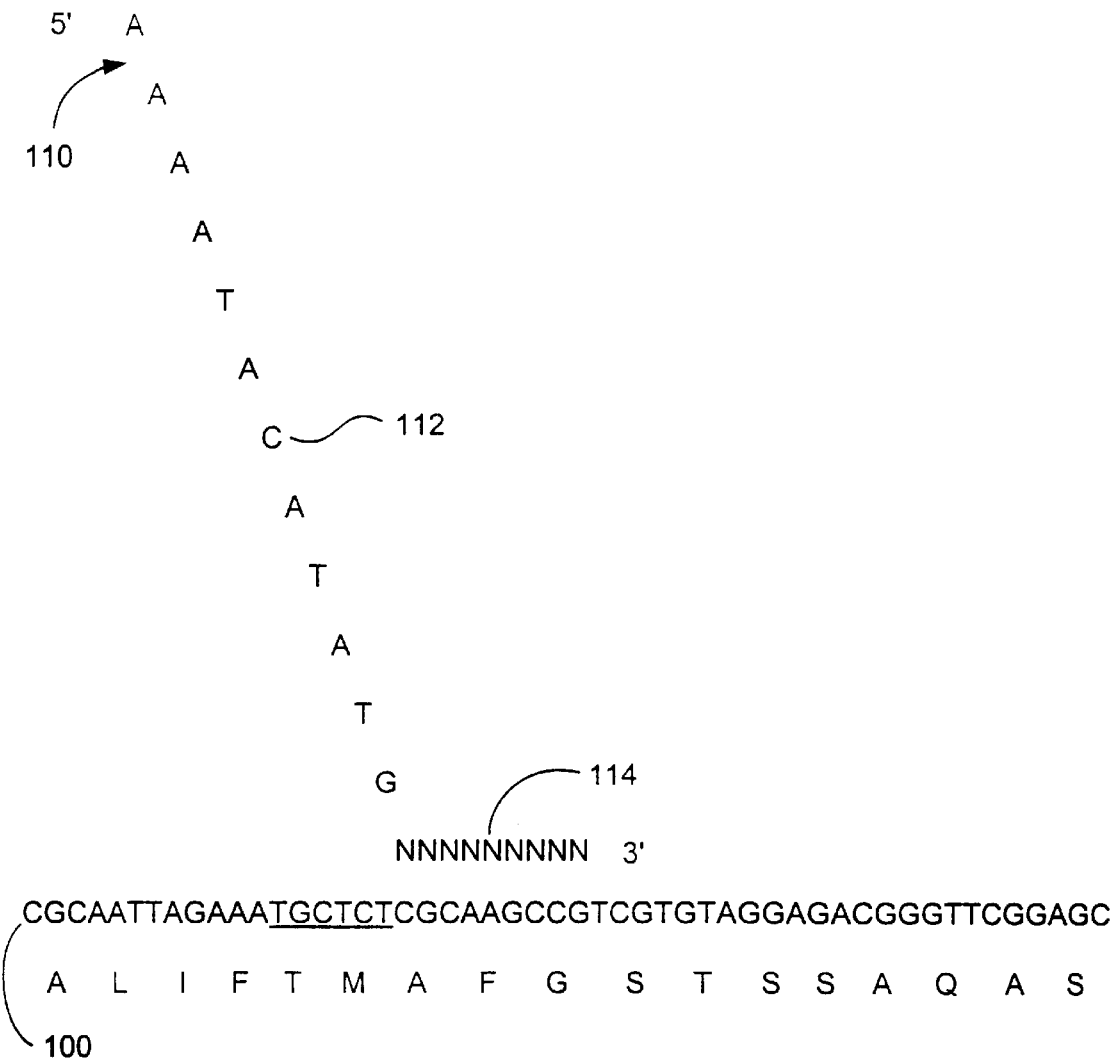
FIG. 2A illustrates an example of a first primer having a fixed sequence containing a NdeI restriction site 5' to an unknown sequence 5'-NNNNNNNNN-3' that anneals to a portion of the antisense strand of a target gene.

FIG. 2A illustrates an example of a first primer according to the present invention. The first primer 110 includes a fixed sequence 112, 5'-AAAATACATATG-3', that includes a NdeI restriction site CATATG and an ATG start codon. The first primer 110 also includes a first unknown sequence 114, 5'-NNNNNNNNN-3', positioned 3' to the fixed sequence 112. The first unknown sequence 114 may anneal to a portion of the antisense strand 100 of a target gene under suitable conditions and be extended by a polymerase during cycles of primer extension amplification.

Figure 2B:
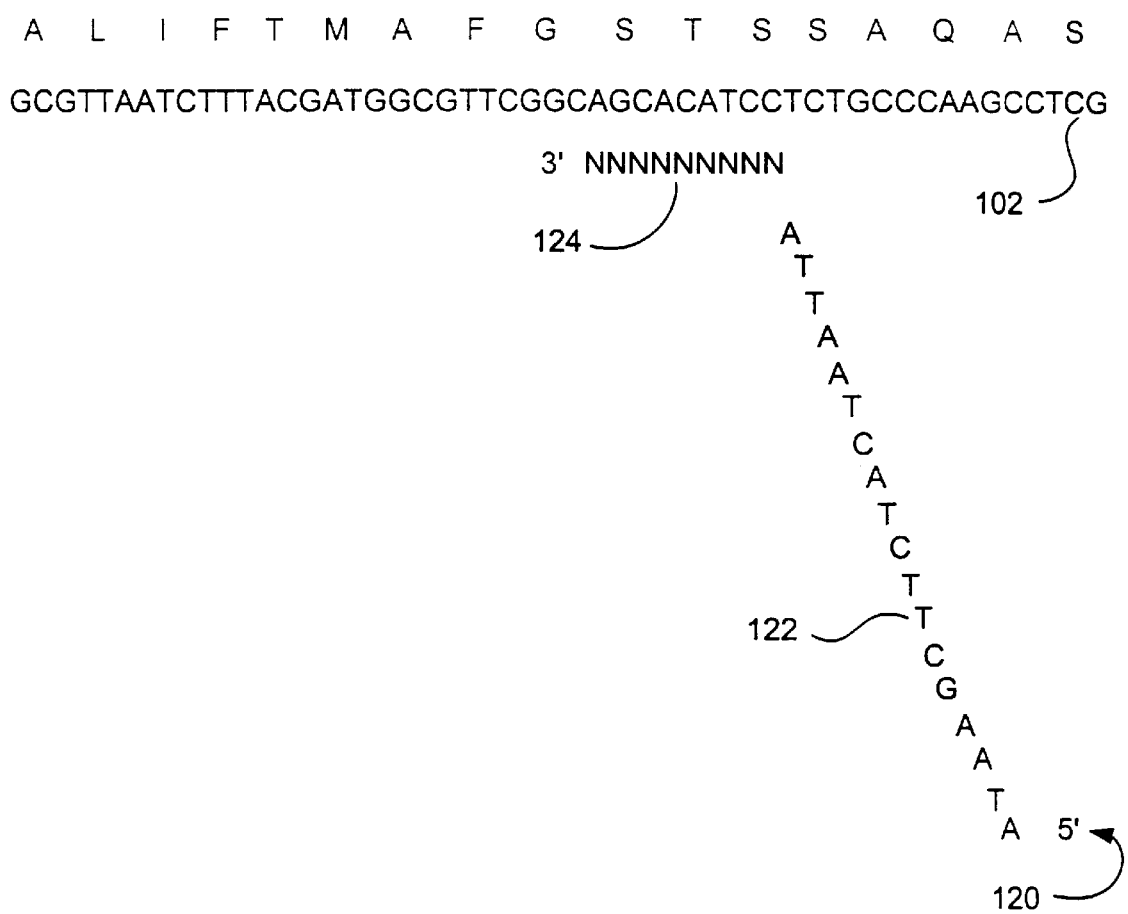
FIG. 2B illustrates an example of a second primer having a fixed sequence containing the complements of the TM and TAG stop codons in separate reading frames and a HindIII restriction site, which are 5' to an unknown sequence 5'-NNNNNNNNN-3' that anneals to a portion of the sense strand of a target gene.

FIG. 2B illustrates an example of a second primer according to the present invention. The second primer 120 includes a fixed sequence 122, 5'-TATTCGAAGATGATTAAT-3', that includes a HindIII restriction site TTCGAA and TAA and TAG stop codons in separate reading frames. The second primer 120 also includes a second unknown sequence 124, 5'-NNNNNNNNN-3', positioned 3' to the fixed sequence 122. The second unknown sequence 124 may anneal to a portion of the sense strand 102 of a target gene under suitable conditions and be extended by a polymerase during cycles of primer extension amplification.

The sequences of the first and second primers are not completely known at the time of amplification. A fixed sequence of the primer is known while the unknown sequence of the primer is unknown.

In the case of primer libraries, the libraries may include a set of primers whose sequences are known and another set of primers whose unknown sequences are unknown. For example, libraries where the unknown sequences of the primers are unknown can be created by chemical synthesis. For example, a library of first primers may be synthesized to include a fixed sequence and an unknown sequence that is a complete randomization of the four nucleosides A, T, C, and G. Such a complete randomization may be achieved by mixing different phosphoramidites at a substantially equal ratio (e.g. A:T:C:G=25%:25%:25%:25%). Complete randomization of the library maximizes the molecular diversity for the unknown sequence at a certain length (e.g. theoretical library size=$4^n$, n: length of the unknown sequence).

Libraries of primers can also be synthesized which have biased randomization. This can be achieved by synthesizing the unknown sequence of the primer in a mixture of conserved base and other phosphoramidites doped into at lower percentages (e.g. below 25%). For example, the mixture may contain a higher percentage of a conserved base (e.g. A at 70%) and a much lower percentage of other bases (T, C and G at 10%, respectively). Such biased randomization allows one to tune the mutagenecity of the target sequence, thereby producing libraries of primers with different degrees of homology to the target sequence.

Optionally, the randomization of the "unknown" portion of the primer can be adjusted to eliminate random combinations of nucleotides that may be prone to structural character unfavorable to template binding. For example, sequences that may result in 'hairpins' may be eliminated from the random nucleotide portion of the oligonucleotide primer family.

The primer libraries can be synthesized by routine solid phase synthesis that incorporates naturally occurring bases such A, T, G, C, I or U, or unnatural bases that may not interfere with the primer extension by polymerase at each position (Barbas, C. F. et al. Angew. Chem. Int. Ed. (1998) 37: 2872–2875).

The primers may be modified with biotin or other detectable markers that may be desirable in the detection, quantification, isolation and purification of the amplification products.

The length of the first and second primers should be of a sufficient length to prime the synthesis of extension products in the presence of a polymerase. The first and second primers are preferably between 10 and 80 nucleotides in length, more preferably between 12 and 60 nucleotides, and most preferably between 15 and 40 nucleotides.

The length of the unknown sequence must be at least 3 nucleotides, preferably between 3 to 70 nucleotides, more preferably between 4 and 50 nucleotides, and most preferably between 5 and 15 nucleotides. It is contemplated that longer oligonucleotides may result in longer insertions and/or deletions. In a library of primers, the first and second primers can have uniform lengths or mixed lengths.

4. Amplification Conditions

The method according to the present invention can be used to tune the degree of mutagenesis of a target sequence. This is achieved by exploiting the structural versatility and dynamics of nucleic acids under different amplification conditions. Annealing and dissociation of an oligonucleotide to a target sequence may be dependent on many factors, such as temperature, pH, ionic strength, $Mg^{2+}$ concentration, etc. In general, heating or high pH (~12) would destabilize (or denature) intra- or inter-molecular base pairing, while lowering the temperature would favor the formation of duplexes (intermolecular interaction) and hairpins (intramolecular interaction). Under suitable conditions an oligonucleotide that is partially complementary to a target sequence may form an imperfect duplex which may contain mismatches, bulges and internal loops. Such duplexes may be stabilized by lowering the temperature or adjusting ionic strength of the solution, i.e. under less stringent conditions. At lower temperature, dynamic breathing of the duplex may be significantly reduced. Therefore, in the presence of polymerase, extension of the oligonucleotide can be achieved even though the oligonucleotide is not completely complementary to the target sequence. A more detailed description of the methodology is described as follows.

The target sequence, the first and second primers can be mixed and denatured at suitable conditions known to one skilled in the art, such as by heating or by alkali treatment. For example, the mixture can be heated to between 85 to 100° C., more preferably between 90 to 95° C., most preferably at about 94° C.

Once denatured, the first and second primers in the sample may be annealed to the target sequence by incubating the mixture under suitable conditions. For example, the sample may be incubated for at least 15 sec. at a temperature below 60° C., more preferably below 55° C., and most preferably below 50° C. The lowering of the temperature from denaturation to annealing may be performed in a ramped, stepwise, or linear manner. Incubation at these lower temperatures is believed to enhance the annealing of the oligonucleotides to the target sequence by stabilizing the imperfect double-stranded complex formed. At lower temperatures, less perfect double-stranded complex can be formed.

In the presence of at least one polymerase, the primers annealed to the target sequence are extended. The sample is incubated in the presence of the polymerase for a sufficient period of time to allow full-length extension.

As the primers are extended, the primers become more complementary to the target sequence, thereby stabilizing the imperfect double-stranded complex formed between the primers and the target sequence. As the primers are extended, it is possible to gradually increase the temperature, preferably to 72° C. Increasing the temperature from below 55° C. to about 72° C. is desirable since TAQ polymerase activity increases to a maximum at around 72° C.

Figure 3:
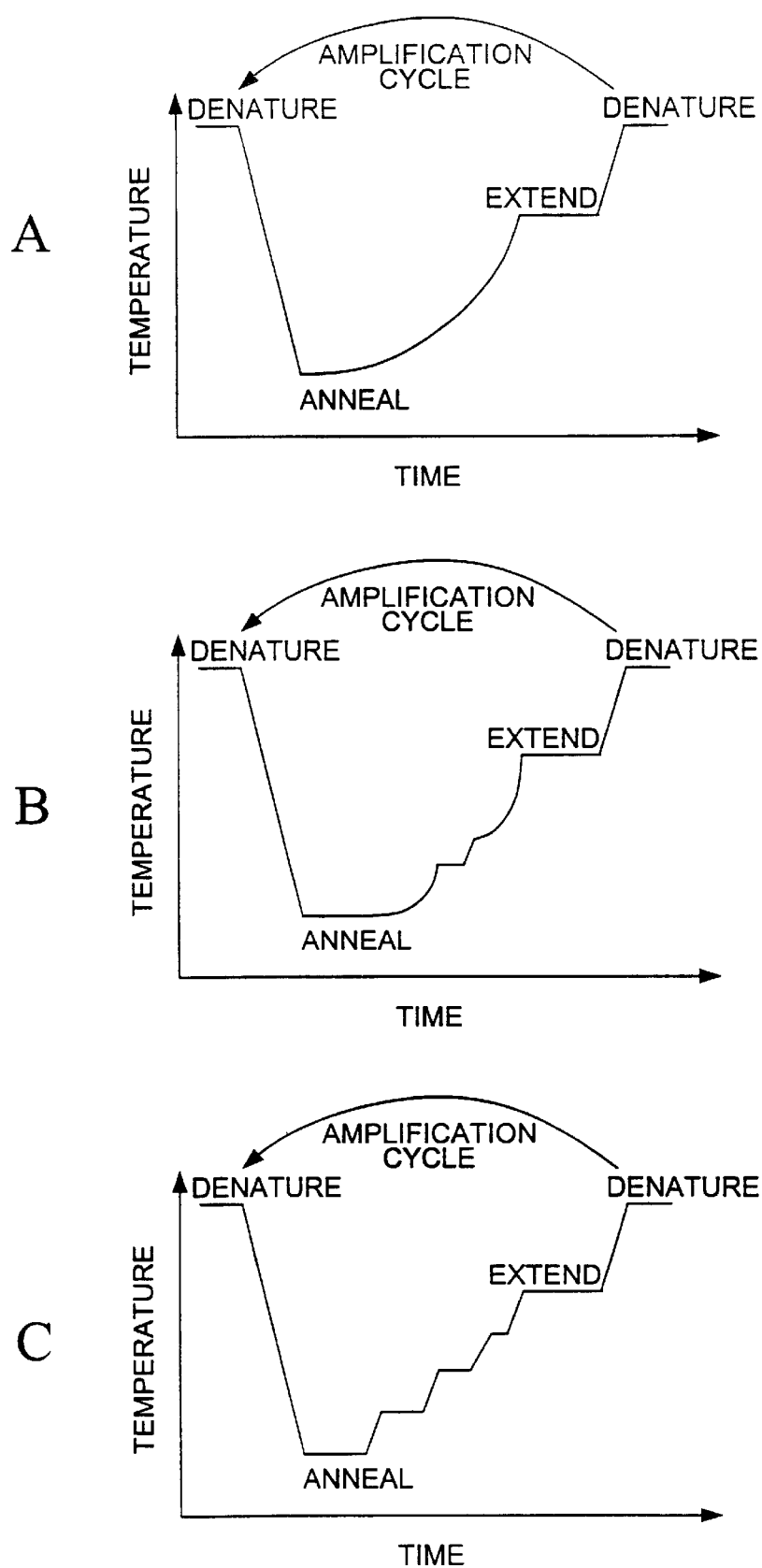
FIGS. 3A–C illustrate three examples of the temperature profiles that may be used in the method.

FIGS. 3A–C illustrate three temperature profiles that may be used for performing amplifications. It is noted that these temperature profiles are merely exemplary and that different temperature profiles may also be used.

As illustrated in FIG. 3A, after the denaturation of the sample, the primers are allowed to anneal to the target at a low temperature. The annealing temperature is then gradually increased until the optimum temperature for the polymerase is reached.

FIG. 3B illustrates another temperature profile for performing an amplification. As illustrated, the annealing temperature is raised by a combination of gradual rises in temperature with temperature plateaus for a period of time.

FIG. 3C illustrates yet another temperature profile for performing an amplification. As illustrated, the annealing temperature is raised in a step-wise manner. As also illustrated, the incubation time after each ramp/step is shorter than previous one. This ramping approach is contemplated to increase the stringency of apposition annealing of the primers to the target sequence, thereby limiting the formation of concatamers, i.e. tandem repeats of the target sequence or the primers.

It is noted that polymerase activity is generally temperature dependent. More specifically, a polymerase will have a maximum level of activity at a certain temperature, that activity decreases as the temperature increases or decreases from the optimal temperature. Given that the amplification is conducted over a range of temperatures, it may be desirable to utilize multiple polymerases where different polymerases are used at different temperatures. For example, a polymerase with optimum activity at a lower temperature (e.g. about 37° C.) can be added into the mixture at the annealing step to enhance extension of the annealed oligonucleotides at low temperatures. Examples of such polymerases include, but are not limited to, the large proteolytic fragment of the DNA polymerase I of the bacterium *E. coli*, commonly known as *Klenow polymerase, E. coli* DNA polymerase I, and bacteriophage T7 DNA polymerase.

Given that multiple cycles of amplification are needed in order to perform the methods of the present invention, it is preferred to use a thermostable polymerase, such as TAQ DNA polymerase derived from the thermophilic bacterium *Thermus aquaticus*, as well as various commercially available high or low fidelity thermostable polymerases such as ACCUTAQ and KLENTAQ from Sigma.

Thermostable polymerases are typically most active at higher temperatures. Hence, in order to extend the primers at lower temperatures, it is necessary to incubate the sample at the lower temperatures for a longer period of time than at higher temperatures. This feature is illustrated in FIGS. 3A–C where the slope of the temperature curve is smaller at lower temperatures than at higher temperatures.

It may be necessary to provide the amplification mixture a sufficient amount of salts such as $Mg^{2+}$, KCl and NaCl, or polyethylene glycol ("PEG"). Cations such as $Mg^{2+}$, $K^+$ and $Na^+$ are believed to bind to DNA and enhance the stability of duplexes. Polymers such as PEG are believed to increase the condensation of DNA and favor the formation of DNA complexes between strands. For example, extra $Mg^{2+}$ may be added to the amplification mixture at a concentration between zero and 100 mM (assuming $Mg^{2+}$ is provided in the polymerase reaction buffer), preferably between 2 and 20 mM.

The amplification may also contain nucleoside triphosphate substrates such as dATP, dCTP, dGTP, dTTP, dITP, ATP, CTP, GTP, UTP in sufficient quantities to support the degree of amplification desired. The amount of deoxyribonucleotide triphosphates substrate required for substantial DNA amplification by primer extension polymerase amplification may be in the range of 50 to 500 mM, preferably in the range of 100 to 300 mM. Optionally, nucleoside triphosphate analogues may be substituted or added to the above mixture, provided that the base pairing, polymerase, and strand displacing functions are not adversely affected to the point that the amplification does not proceed to the desired extent.

5. Isolation and Characterization of Mutagenized Polynucleotides

The library of mutagenized polynucleotides formed after multiple amplification cycles may be analyzed or characterized by using any of a variety of methods well known in the art. For example, the library may be sequenced, restriction digested, electrophoresed, or hybridized against a reference nucleic acid molecules. In one embodiment, the amplification reaction mixture is subjected to agarose gel electrophoresis, stained with DNA binding dyes such as ethidium bromide, the amplification product may appear as a □smear□ or "cloud" under UV light, representing randomly mutagenized target sequences.

The mutagenized polynucleotides may be isolated from the amplification products by using methods known in the art, such as gel eletrophoresis, gel filtration, ion exchange chromatography, affinity chromatography and magnetic beads. The isolated DNA may be digested with restriction enzymes on the sites that are carried by the first and second primers and incorporated into the mutagenized target sequence to yield fragments suitable for subcloning into a vector. The vector used for cloning may not be critical so long as the DNA fragment can be ligated into the vector. Alternatively, the isolated DNA may be directly subcloned into a vector by using the commercially available cloning kits (e.g. TA cloning kits from Invitrogen). Each clone may be sequenced by using conventional dideoxynucleotide sequencing method or by using an automatic sequencer.

6. Expression of Mutagenized Polynucleotides

The mutagenized polynucleotides may also be cloned into expression vectors that comprise transcription and translation signals next to the site of insertion of the polynucleotides to allow expression of the polynucleotides in host cells. Alternatively, the mutagenized polynucleotides may carry transcription and translation initiation and termination signals that control the expression.

The host cells for expression of the mutagenized polynucleotides may be prokaryotic and/or eukaryotic cells. Examples of prokaryotic cells include but are not limited to those of bacterial cell types, both gram-negative and gram-positive, such as *Escherchia coli*, Bacillus, Penicillium, Streptomycetes and Salmonella. Examples of eukaryotic cells include but are not limited to yeast, algae, fungi, plant, insect, mammalian (e.g. mouse, hamster, primate, human) cells, both cell lines and primary cultures. Plant cells include maize, rice, wheat, cotton, soybean, sugarcane, tobacco, and arabidopsis. Mammalian cells include stem cells, including embryonic stem cells, zygotes, fibroblasts, lymphocytes, kidney, liver, muscle, and skin cells.

The choice of host cell for expression of the mutagenized polynucleotides depends on several factors including the molecular characteristic of the mutant to be screened. For example, if the mutant protein expressed confers resistance to certain antibiotics, the host cell may be a suitable bacterial cell. If the mutant protein expressed confers resistance to apoptosis (programmed cell death), a mammalian cell may be an appropriate choice for the host cell.

7. Screening of Mutagenized PolyDeptides

The mutant protein may be selected by using various methods, depending on its desired function. Selection may be achieved by using a selectable marker, easily assayed enzymes such as beta-galactosidase, luciferase, chloramphenicol acetyl transferase and secreted embryonic alkaline phosphatase; proteins for which immunoassays are readily available such as hormones and cytokines; proteins which confer a selective growth advantage on cells such as adenosine deaminase, aminoglycoside phosphotransferase, thymidine kinase, xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin. Screening can also be done by observing such aspects of growth as colony size, halo formation, or by using automatic screening devices such as fluorescence activated cell sorter (FACS) and automatic ELISA.

In addition, screening for desired affinity to a ligand may be accomplished by binding to an affinity column or a solid support. Hydrolytic enzymes (e.g. proteases, amylases) can be screened by including the substrate in an agar plate and scoring for a hydrolytic clear zone or by using a colorimetric indicator (Steele et al., Ann. Rev. Microbiol. (1991) 45: 89–106).

A phage display system may also be used to screen for mutant protein with desired function. The mutagenized target sequences may be cloned into a phage DNA at a site which results in transcription of a fusion protein. The phage containing the recombinant DNA undergoes replication in bacterial cells. The leader sequence of the fusion protein directs the transport of the fusion protein to the tip of the phage particle. Thus the fusion protein which is particularly encoded by mutagenized target sequence is displayed on the phage particle for detection and selection by methods described above.

EXAMPLE

The gene encoding a penicillinase from *Bacillus licheniformis* was used as a target to be randomly mutagenized. By randomly mutating the enzyme, isozymes which show altered hydrolytic activity and/or specificity against various penicillins and cephalosporins may offer clues to 1) how antibiotics can be designed to thwart the inevitable evolution towards β-lactamases which render pathogenic bacteria resistant to drug therapy, and 2) offer further information for the study of protein structure-function relationships.

The gene encoding the *Bacillus licheniformis* was isolated from a plasmid pELB1. The plasmid pELB1 is a pBR322 derivative, containing the "exolarge" form of the *B. licheniformis* β-lactamase gene, utilizing the *Bacillus amyloliquefaciens* promoter and subtilisin signal sequence, and Bacillus and *E. coli* origins of replication (Ellerby, L. M., Escobar, W. A., Fink, A. L., Mitchinson C., Wells JA (1990) *Biochemistry*, June 19; 29(24):5797–806).

pELB1 was digested with restriction enzymes NdeI (incorporating the 'START' codon ATG) and DraIII, a site unique to the plasmid immediately downstream of the gene's TAA (STOP) codon. This double-stranded polynucleotide fragment encodes a 273 amino acid β-lactamase.

The first and second primers were designed to incorporate the START and STOP codons, respectively. The first primer includes the restriction site NdeI (which incorporates the ATG START condon in the fixed sequence region. The second primer includes a STOP codon and the restriction site DraIII. The START and STOP codons were designed to be recognized in *E. coli* strain BL21 (DE3). Examples of the 5'- and 3'-primers used are listed below.

```
5'-primer having a NdeI site
(underlined):                            [SEQ ID No. 1]
5'-AAAATACATATGNNNNNNNNNN-3'

3'-primer including STOP codon and
DraIII site (underlined):                [SEQ ID No. 2]
5'-ATAAGTGCTTCACTACTAATTANNNNNNNNNN-3'
```

Amplifications of the β-lactamase gene were carried out, using synthetic primers including a unknown sequence that randomly incorporates either A, T, G, or C, nucleoside tri-phosphates at each position. These randomly sequenced primers formed a library of oligonucleotides with various sequences which were used in subsequent amplifications designed to randomly mutate the β-lactamase gene template.

The amplifications were performed using a polymerase catalyzed primer extension. During the amplifications, the isolated β-lactamase gene template and the libraries of the first and second primers can interact and anneal with each other to form imperfect double-strand sequences. Several thermostable polymerases including Vent, Taq and Ultma (Perkin Elmer Co. CA) DNA polymerase were used under varying salt conditions, typically at 5 to 15 mM $MgCl_2$. Table I lists concentrations of various reagents for an exemplary amplification of the present invention.

A typical cycle of amplification was programmed to run as follows. In order to enhance annealing of the random oligonucleotides over the entire length of the gene template, and allow the annealing despite significant mismatches, low annealing temperatures were used initially (e.g. 40° C.), which were ramped upward to the optimum temperature of 72° C. for a typical thermostable DNA polymerase. Synthesis of polynucleotides via primer extensions was followed by denaturation at 90° C. Up to 45 cycles were employed to generate randomized products.

TABLE I

| Reagent | Volume (µL) | Final concentration (/100 µL) |
|---|---|---|
| Sterile $H_2O$ | 62.0 | N/A |
| Template | 2.0 | ~$10^6$ copies |
| 10× Ultma Polymerase Buffer | 10.0 | 1× |
| 50 mM $MgCl_2$ | 15.0 | 7.5 µM |
| 10 mM dATP | 2.0 | 200.0 µM |
| 10 mM dCTP | 2.0 | 200.0 µM |
| 10 mM dGTP | 2.0 | 200.0 µM |
| 10 mM dTTP | 2.0 | 200.0 µM |

TABLE I-continued

| Reagent | Volume (μL) | Final concentration (/100 μL) |
|---|---|---|
| 5' Primer | 1.0 | 0.5 μM |
| 3' Primer | 1.0 | 0.5 μM |
| DNA Polymerase (Ultma) | 1.0 | 1 U |

Figure 4:
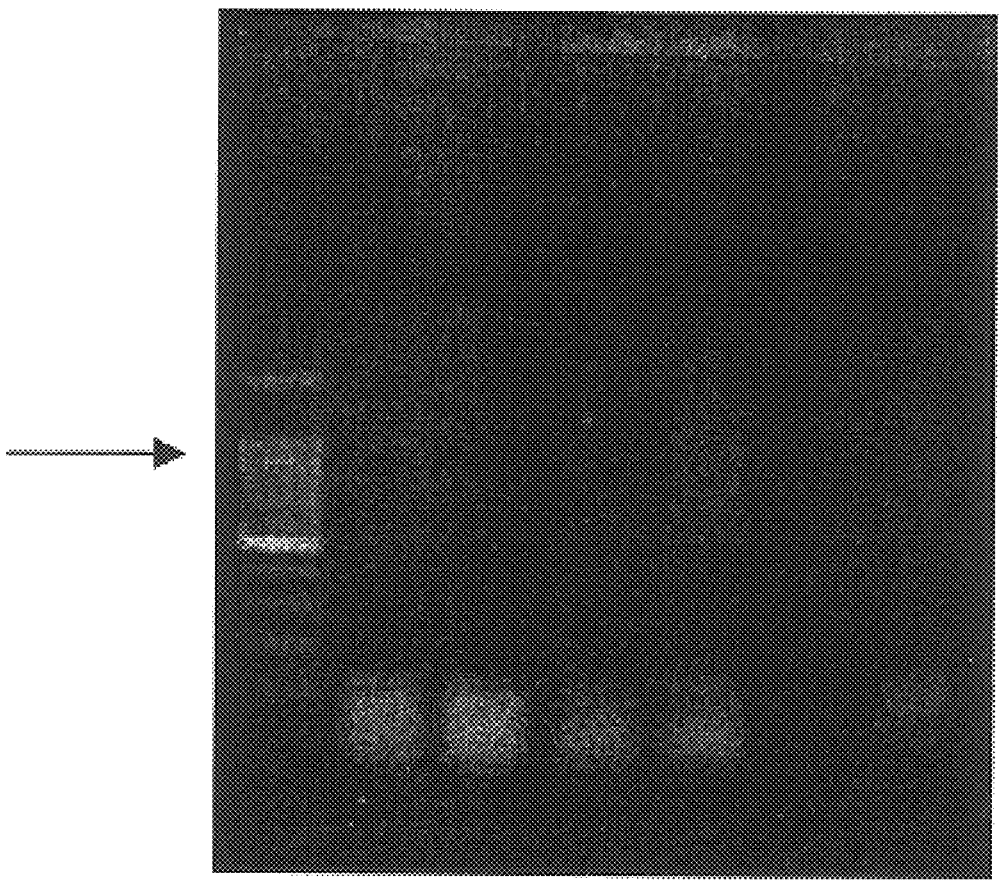
FIG. 4 illustrates mutagenesis reaction products separated by agarose gel. Lane 1 corresponds to 100 bp DNA molecular weight marker. Lanes 2 to 7 correspond to reaction products as a resulting of increasing primer/template (target sequence) ratios.

The amplification products were separated using gel electrophoresis, stained with ethidium bromide, and visualized under UV light (FIG. 4). As shown in FIG. 4, lanes 2 to 5 correspond to reaction products as a result of increasing primer/template (target sequence) ratios. Lanes 2, 3, 4, and 5 correspond to primer/template ratios increased 1×, 10×, 100×, 1000×, respectively. Reaction components for Lane 5 are listed in Table I.

Lanes 6 and 7 show amplification products of reactions in which 2 μM $Mg^{2+}$ was included. The electrophoresed DNA products from the reactions including the first primer (5'-AAAATACATATGNNNNNNNNN-3') [SEQ ID No. 1] and second primer (5'-ATMGTGCTTCACTACTAATTANNNNNNNNN-3') [SEQ ID No. 2] appear as "smears" (FIG. 4, lanes 4 and 5, respectively). Compared to the 100 bp (base pairs) molecular weight marker shown in lane 1 of FIG. 4, the "smears" indicate that the amplified products vary in size, predominantly shorter than the size of the original β-lactamase gene template (about 1000 bp. in length, indicated by an arrow in FIG. 4). This is indicative of expected random truncation of the target gene.

Figure 5:
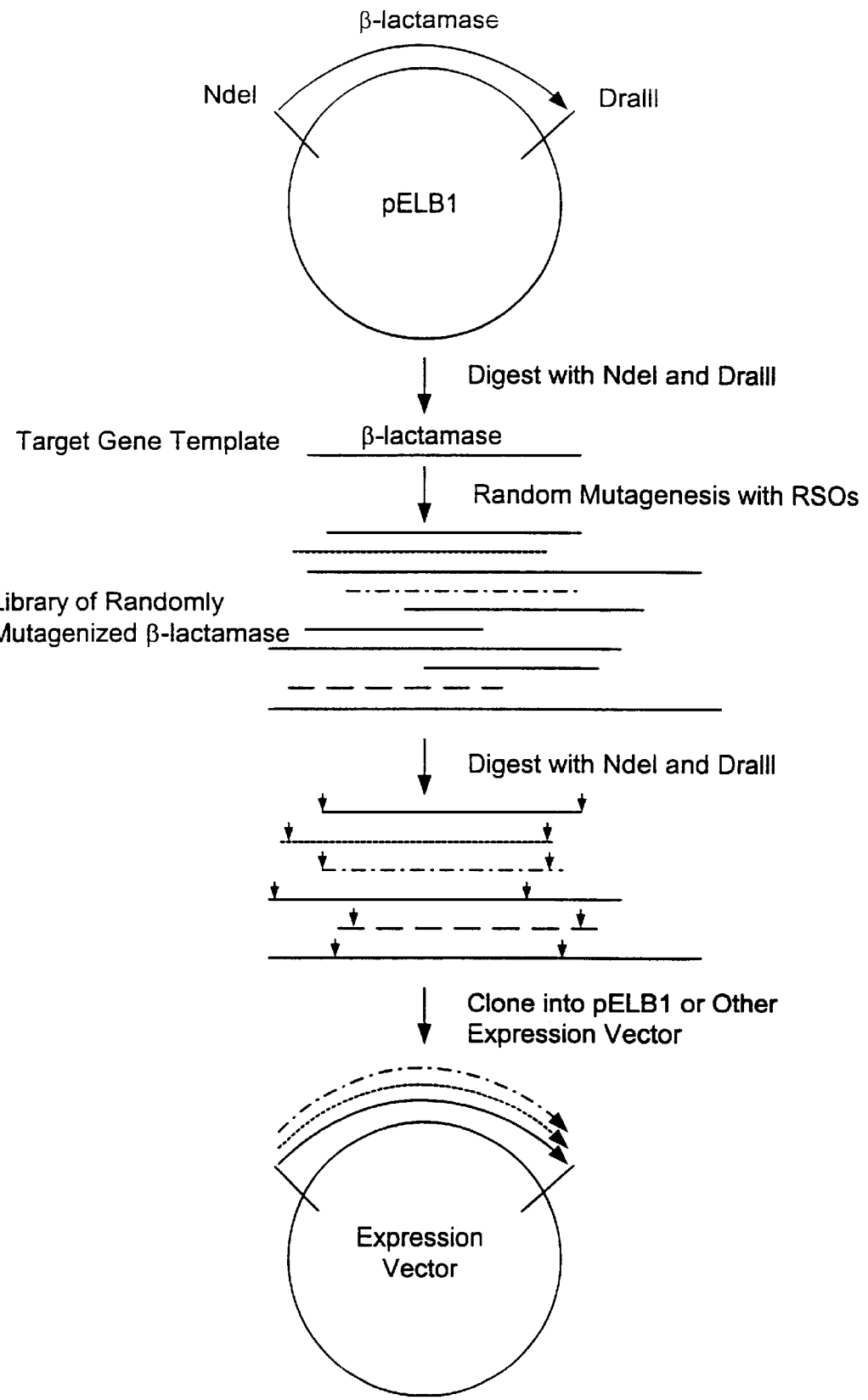
FIG. 5 schematically illustrates subcloning of a library of mutagenized target gene sequences into a bacterial expression vector.

Amplification products are extracted from the gel by methods know to those of the art (or, e.g. Qiagen). The isolated DNA is digested with the NdeI and DraIII restriction endonucleases for efficient subsequent subcloning, and ligated (using a T4 DNA ligase) into a suitable expression vector (e.g. pELB1, FIG. 5). The products of the ligation reactions are used to transform E. coli host such as strain BL21(DE3).

Transformant constructs containing encoded polypeptides which confer desired characteristics to the host cells (e.g. to be able to proliferate under specified conditions) can be isolated and purified. Specific changes which result in the appearance of desired characteristics can be identified by sequence analysis of the selected construct(s).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and example be considered as exemplary only, with a true scope and spirit of the invention being indicated by the claims.

What is claimed is:

1. A method for producing a library of mutagenized polynucleotide from a target sequence comprising:

(a) taking a sample comprising (i) a target sequence including a section to be mutagenized, (ii) a library of first primers where the first primers include a first fixed sequence and a first unknown sequence 3' to the first fixed sequence, the first unknown sequence varying within the library of first primers, and (iii) a library of second primers where the second primer include a second fixed sequence that differs from the first fixed sequence, and a second unknown sequence 3' to the second fixed sequence, the second unknown sequence varying within the library of second primers;

(b) performing one or more cycles of primer extension amplification on the sample in the presence of at least one polymerase such that a member of the library of the first primers is extended relative to the target sequence; and (c) performing one or more additional cycles of primer extension amplification on the sample such that a member of the library of the second primers is extended relative to the first primer that was extended in step (b) to form the library of mutagenized polynucleotides.

2. The method according to claim 1 wherein at least one of the first or second unknown sequences is unknown at the time of primer extension amplification.

3. The method according to claim 1 wherein the target sequence has a sequence which is at least partially unknown at the time of primer extension amplification.

4. The method according to claim 1, wherein the target sequence has a sequence which is the CDR of an antibody.

5. The method according to claim 1, wherein the target sequence has a sequence encoding a single-chain antibody.

6. The method according to claim 1 wherein the first and second fixed sequences include at least one restriction site.

7. The method according to claim 1 wherein one of the fixed sequence of the first and second primers includes an ATG or a GTA sequence and the fixed sequence of the other primer includes a sequence encoding one or more translation stop codons.

8. The method according to claim 1 wherein the first or second primers include one or more inosines at the 3' end penultimate and ultimate positions.

9. The method according to claim 1 wherein the length of the first and second primers is between 10 and 80 nucleotides.

10. The method according to claim 1 wherein the first or second unknown sequence has a length between 3 and 70 nucleotides.

11. The method according to claim 1 wherein the first or second unknown sequence has a length between 4 and 50 nucleotides.

12. The method according to claim 1 wherein the first or second unknown sequence has a length between 5 and 20 nucleotides.

13. The method according to claim 1 wherein the first or second unknown sequence further includes a sequence encoding one or more specific amino acid residues.

14. The method according to claim 13 wherein the one or more specific amino acid residues are conserved amino acid residues of the protein encoded by the target sequence.

15. The method according to claim 1 wherein at least a portion of the multiple cycles of primer extension polymerase amplification is performed such that extension by the polymerase is at least partially performed at a temperature below 70° C. for at least 30 sec.

16. The method according to claim 1 wherein at least a portion of the multiple cycles of primer extension polymerase amplification is performed such that extension by the polymerase is at least partially performed at a temperature below 60° C. for at least 30 sec.

17. The method according to claim 1 wherein at least a portion of the multiple cycles of primer extension polymerase amplification is performed such that extension by the polymerase is at least partially performed at a temperature below 50° C. for at least 30 sec.

18. The method according to claim 1 wherein at least a portion of the one or more cycles of primer extension polymerase amplification is performed such that extension by the polymerase is at least partially performed by heating the amplification reaction mixture from temperature of between 30° C. to 50° C. to a temperature between 65° C. to 75° C. over the course of at least 30 sec.

19. A method for producing mutagenized polynucleotide from a target sequence comprising:
(a) taking a sample comprising
(i) a target sequence including a section to be mutagenized,
(ii) a first primer where the first primer includes a first fixed sequence and a first unknown sequence 3' to the first fixed sequence, and
(iii) a second primer where the second primer includes a second fixed sequence that differs from the first fixed sequence, and a second unknown sequence 3' to the second fixed sequence;

(b) performing one or more cycles of primer extension amplification on the sample in the presence of at least one polymerase such that the first primer is extended relative to the target sequence; and (c) performing one or more additional cycles of primer extension amplification on the sample such that the second primer is extended relative to the first primer that was extended in step (b) to form the mutagenized polynucleotide.

20. The method according to claim 19 wherein the first or second unknown sequence is unknown at the time of primer extension amplification.

21. The method according to claim 19 wherein the target sequence has a sequence Which is at least partially unknown at the time of primer extension amplification.

22. The method according to claim 19 wherein the first and second fixed sequences include at least one restriction site.

23. The method according to claim 19 wherein one of the fixed sequence of the first and second primers includes an ATG or a GTA sequence and the fixed sequence of the other primer includes a sequence encoding one or more translation stop codons.

24. The method according to claim 19 wherein the length of the first and second primers is between 10 and 80 nucleotides.

25. The method according to claim 19 wherein the first or second unknown sequence has a length between 3 and 70 nucleotides.

26. The method according to claim 19 wherein the first or second unknown sequence has a length between 4 and 50 nucleotides.

27. The method according to claim 19 wherein the first or second unknown sequence has a length between 5 and 20 nucleotides.

28. The method according to claim 19 wherein the first or second unknown sequence further includes a sequence encoding one or more specific amino acid residues.

29. The method according to claim 28 Wherein the one or more specific amino acid residues are conserved amino acid residues of the protein encoded by the target sequence.

30. The method according to claim 19 wherein at least a portion of the multiple cycles of primer extension polymerase amplification is performed such that extension by the polymerase Is at least partially performed at a temperature below 70° C. for at least 30 sec.

31. The method according to claim 19 wherein at least a portion of the multiple cycles of primer extension polymerase amplification is performed such that extension by the polymerase is at least partially performed at a temperature below 60° C. for at least 30 sec.

32. The method according to claim 19 wherein at least a portion of the multiple cycles of primer extension polymerase amplification Is performed such that extension by the polymerase Is at least partially performed at a temperature below 50° C. for at least 30 sec.

33. The method according to claim 19 wherein at least a portion of the one or more cycles of primer extension polymerase amplification Is performed such that extension by the polymerase is at least partially performed by heating the amplification reaction mixture from temperature of between 30° C. to 50° C. to a temperature between 65° C. to 75° C. over the course of at least 30 sec.

* * * * *